United States Patent [19]

Mistretta

[11] Patent Number: 5,405,110
[45] Date of Patent: Apr. 11, 1995

[54] CATHETER HOLDING APPARATUS

[75] Inventor: Charles A. Mistretta, Madison, Wis.

[73] Assignee: Wisconsin Alumni Research Foundation, Madison, Wis.

[21] Appl. No.: 134,016

[22] Filed: Oct. 8, 1993

[51] Int. Cl.⁶ ............................................. F16L 3/00
[52] U.S. Cl. .............................. 248/122; 128/DIG. 6; 604/174
[58] Field of Search .................. 248/121, 122, 514, 49; 128/DIG. 6; 604/174, 177, 178

[56] References Cited

U.S. PATENT DOCUMENTS

| 2,266,230 | 12/1941 | Mazzeo et al. | 128/327 |
|---|---|---|---|
| 2,266,231 | 12/1941 | Mazzeo | 604/174 X |
| 2,463,400 | 3/1949 | Lowe | 604/174 X |
| 2,723,665 | 11/1955 | Goldsmith | 120/DIG. 6 X |
| 3,293,789 | 12/1966 | Pack | 248/514 X |
| 3,625,210 | 12/1971 | Mikkelson | 128/214 R |
| 3,881,269 | 5/1975 | Timmons | 248/514 X |
| 3,971,538 | 7/1976 | Marvich | 248/278 |
| 4,212,297 | 7/1980 | Frosch | 604/174 X |
| 4,671,477 | 6/1987 | Cullen | 248/122 |
| 4,955,864 | 9/1990 | Hajduch | 604/174 |
| 5,054,723 | 10/1991 | Arnold | 604/174 |

Primary Examiner—J. Franklin Foss
Attorney, Agent, or Firm—Quarles & Brady

[57] ABSTRACT

Some patients have an catheter extending from an upper arm in order to administer intravenous pharmaceuticals. A clamping apparatus rigidly holds an end of the catheter during pharmaceutical administration thus allowing the procedure to be performed using only the patient's free hand. The apparatus has a base from which a support member extends. A mechanism enables the support member to be positioned at a number of angles with respect to the base. A catheter clamp can be attached along the support member in a number of positions. This mechanism allows the position of the clamp to be varied in order to accommodate patients having arms of different size.

13 Claims, 2 Drawing Sheets

CATHETER HOLDING APPARATUS

BACKGROUND OF THE INVENTION

The field of invention relates to devices for holding catheters which are implanted into a patient and extend externally from an arm.

Patients, such as those suffering from cancer, are often sent home from hospitals with the need for continued administration of intravenous drugs. One common technique for administering such drugs is to have a peripheral inserted central catheter (PICC) implanted in a vein and extending through an incision in the patient's upper arm. The drugs are administered by injection into the catheter from which they are drawn into the vein of the patient.

Because the catheter is inaccessible to the hand on the arm having the catheter, the patient is unable to perform the operations of flushing the catheter and administering the drugs without the assistance of another person. Thus, the patient is confronted with the need for home nursing or help from other individuals in administering the drugs in this manner.

It is therefore desirable to provide a mechanism that will assist the patient in administering the drugs with only the hand on the arm which does not have the catheter.

SUMMARY OF THE INVENTION

It is an object of the present invention to provide a device for holding a catheter or other tube in a rigid position so that the patient can introduce pharmaceutical into the catheter using only one hand.

Another object is to provide such a catheter holding apparatus which can be adjusted depending on the size of the patient's arm.

These objectives are satisfied by an apparatus with a base on which the user can rest the arm to hold the base on a work surface. A mechanism attaches a rod to the base in a manner that allows the rod to be rigidly positioned at a plurality of angles in a plane that is transverse to the plane of the base. A clamp for grasping a catheter extends toward the patient's arm and can be adjusted into different positions along the rod. The adjustability of the rod angle and clamp position enables the apparatus to accommodate patients with widely varying arm sizes.

The weight and pressure exerted by the arm in which the catheter is implanted holds the clamping apparatus in place on the work surface. The rigid positioning of the rod and the clamp with respect to the base holds the catheter in place while the patient uses only the single free hand to administer a pharmaceutical through a tube.

DETAILED DESCRIPTION OF THE INVENTION

Figure 1:
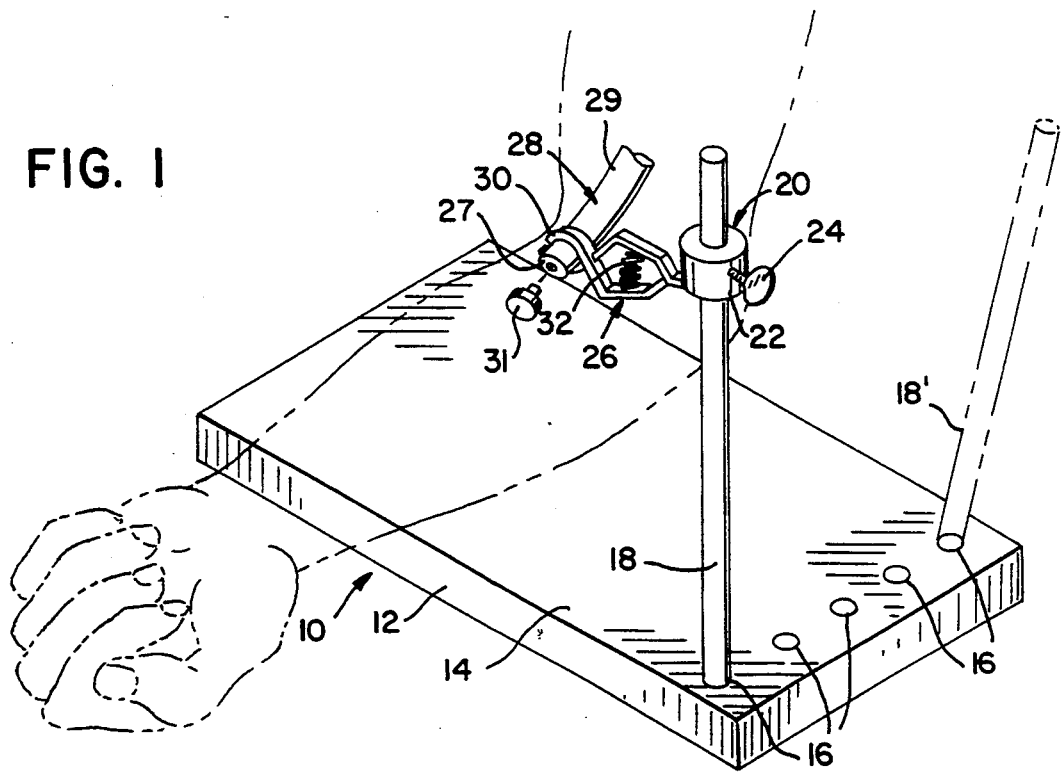
FIG. 1 is an isometric view of a first embodiment of the present invention.

With initial reference to FIG. 1, a catheter clamping apparatus 10 comprises a flat rectilinear base 12 having a major surface 14 which is the upper surface of the base when it is placed on a work surface. A patient using the apparatus 10 places a fore arm on the base 12 to hold the base in place during use. A plurality of circular apertures 16 extend from the upper surface 14 into the base 12 with the longitudinal axis of each aperture 16 being at a different angle with respect to the major surface 14.

A support member such as a circular rod 18 can be positioned in any of the apertures 16. The diameter of rod 18 is approximately equal to the diameter of the apertures 16 so that the rod fits snugly within each of the apertures to be rigidly held in place. By placing the rod 18 in the different apertures, the angle of the rod with respect to the base 12 can be varied as shown by the phantom representation of a rod 18'. The angular variation of the rod adapts the clamping apparatus 10 to patients with different size arms. Although the support member is illustrated as a circular cylindrical rod 18, it may have a square, oval, or other shape cross section with a corresponding change in the shape of apertures 16.

A catheter clamp 20 has a ring 22 with a circular aperture therethrough which receives the rod 18. This aperture is slightly larger in diameter than rod 18, thus enabling the ring to slide easily along the rod. A bolt 24 with a large head, that can be manipulated easily by a patient's fingers, is threaded into a transverse hole in the ring 22. The bolt 24 can be tightened against rod 18 to hold the clamp 20 in a desired location along the rod. A spring-loaded pincher clamp 26 is fixedly attached to the ring 22 for receiving a connector 27 at the end of a peripheral inserted central catheter 28 projecting from the upper arm of the patient. Specifically, the pincher clamp 26 has a set of jaws 30 which hold the catheter connector 27 in place preventing rotation of the of the catheter 28 about its axis. This may be accomplished by properly sizing the jaws 30 and by selection of the spring 32 so that it will exert an appropriate amount of force on the catheter connector 27. The connector 27 is more rigid than the flexible tubing 29 of the catheter 28 and thus is able to withstand the force of pincher clamp 26 without collapsing the central bore of the catheter. FIG. 1 illustrates the catheter connector 27 with its cap 31 removed.

By varying the angles of the apertures 16, the rod 18 can be tilted at different angles with respect to the base. In addition, the clamp 20 can be placed at different locations along the rod. These adjustment mechanisms enable pincher clamp jaws 30 to be located to hold the catheter tube 28 at a convenient point above the user's arm, even though the arms of patients vary widely in size.

Figure 2:
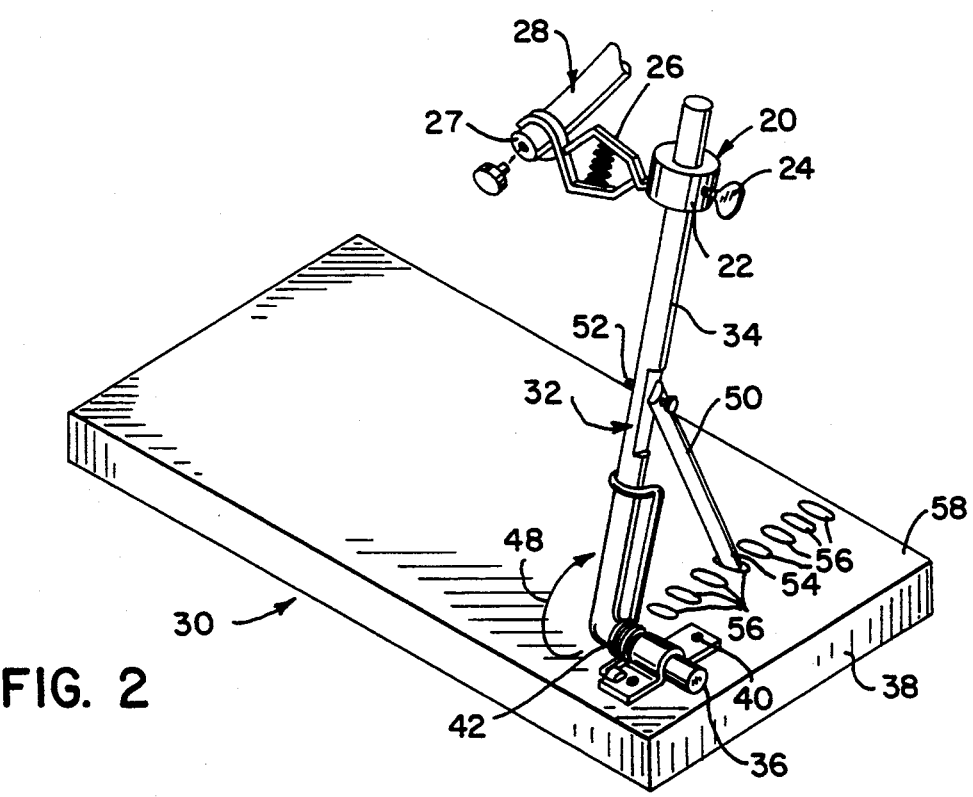
FIG. 2 is an isometric representation of a second embodiment of he present invention.

FIG. 2 illustrates another catheter clamp assembly 30 according to the present invention. An L-shaped support member 32 has an long leg 34 and a relatively short leg 36. The long leg 34 extends through the ring 22 of the catheter clamp 20 which is adjustable to various positions along the long leg 34.

Figure 3:
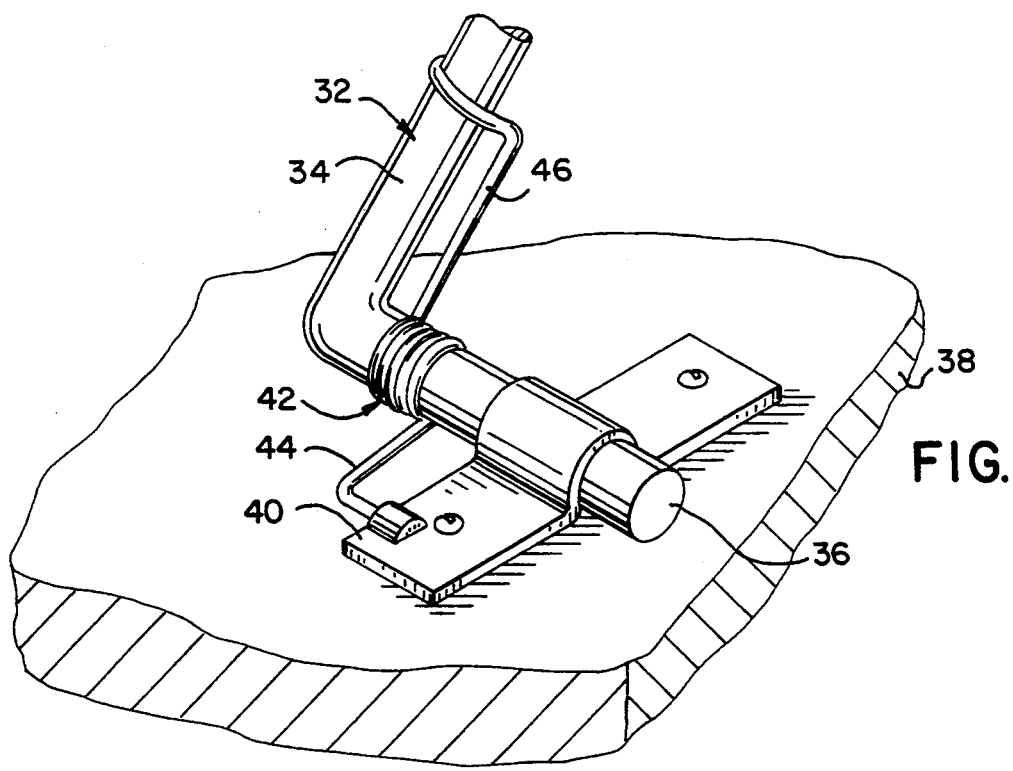
FIG. 3 shows an enlarged portion of part of the mechanism in FIG. 2.

With reference to FIGS. 2 and 3, the short leg 36 of support member 32 is attached to a base 38 by a bracket 40 that is fixed to a major surface of the base by screws. The bracket 40 allows the short leg 36 to rotate against the base 38, thus permitting the support member 32 to pivot up and down. A torsion spring 42 is wrapped around the short leg 36 of the support member 32 between the long leg 34 and bracket 40. One end 44 of the spring 42 is attached to the bracket and the other end 46 is wrapped around the long leg 34. The torsion spring 44 applies a force which biases the support member 32 in a rotational direction indicated by arrow 48.

A strut 50 is pivotally attached by a pin 52 to the long leg 34 of support member 32. The remote end 54 of strut 50 can be placed into different indentations 56 in the upper surface 58 of base 38 to adjust the angle of the support member with the base. A set of ratchet teeth or other mechanism alternatively can be attached to or formed in upper surface 58 in place of indentations 56 to provide stops for the strut 50. Once the strut 50 is positioned in an indentation 56, the support member 32 is held in place against the pivotal force applied by spring 42. This mechanism rigidly hold the catheter 28 in place relative to the patient's arm. When not in use the support member 32 and strut 50 can be collapsed against the surface of base 38.

By positioning the strut 50 in different ones of the indentations 56, the relative angle of the long leg 34 with respect to the upper surface 58 of the base can be varied according to the size of the arm of the patient using the apparatus 30. Adjustment of this angle, plus the adjustment of the clamp 20 along the support member 32 enables the position of the clamp to be varied to accommodate different size patient arms. This enables the catheter 28 to be held in a fixed position that is satisfactory for the introduction of a pharmaceutical by the patient.

Figure 4:
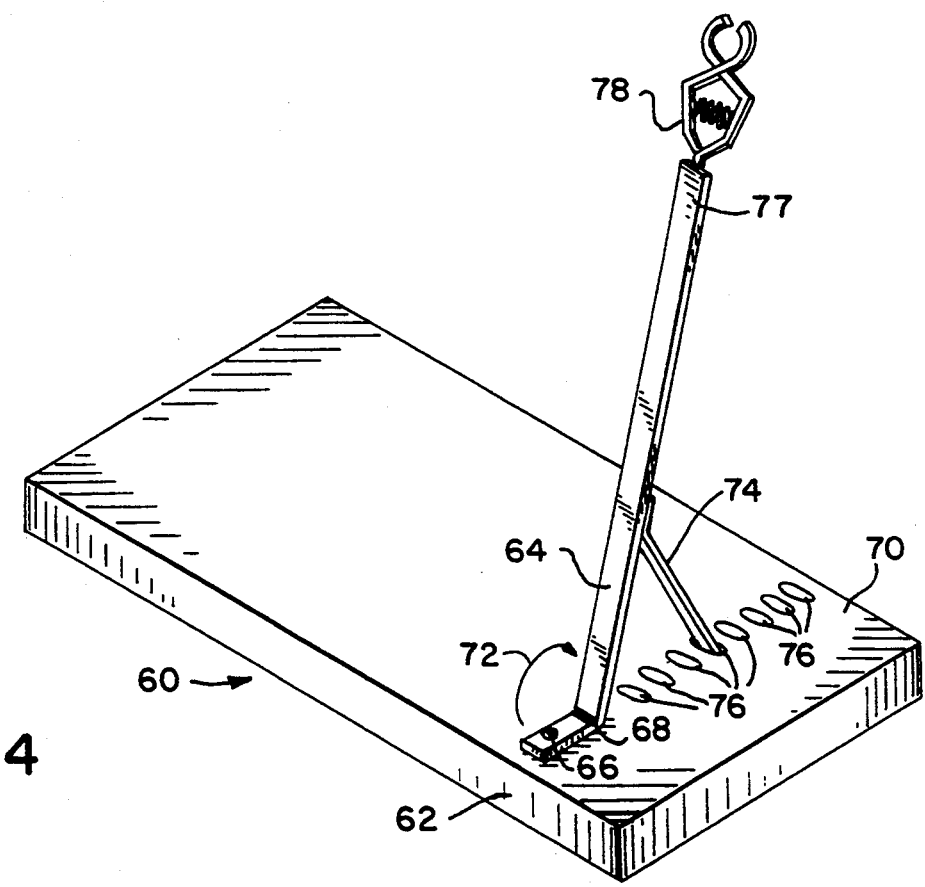
FIG. 4 an isometric representation of a third embodiment of the present invention.

FIG. 4 illustrates another embodiment 60 of the present catheter holding apparatus. A base 62, similar to base 30 in FIG. 2, has a rectangular plastic support element 64 attached to it by a screw 66 or other suitable means. A flexible joint 68 allows the support element 64 to be bent away from the surface 70 of base 62. The elasticity of the plastic material resiliently biases the support element 64 toward the base 62 in rotational direction indicated by arrow 72. Alternatively, the support member 64 can be attached to the base 62 by a hinge and a device the biases the support member in the direction of arrow 72.

A strut 74 is attached at one end to the support member 64 in a manner that allows the strut to pivot with respect to the support member. By pivoting the strut 74, its remote end can be placed into different ones of a plurality indentations 76 in the upper surface 70 of base 62. As with the embodiment in FIG. 2, the indentations 76 can be replaced with other types of stops for the strut 74. The strut 74 resists the elastic force that pivotally biases support member 64 in the direction of arrow 72.

A spring-loaded pincher clamp 78 is fixedly attached to an end 77 of support member 64 that is remote from the base 62. In use, the pincher clamp 78 receives the connector 27 at the end of catheter 28 to rigidly hold the catheter while the patient administers a pharmaceutical.

I claim:

1. An apparatus for enabling a patient, with a tube extending from an arm, to administer a pharmaceutical through the tube, said apparatus comprising:
   a base having a surface on which the patient rests the arm during use of the apparatus;
   a support member extending from said base and having a rigid section with a longitudinal axis;
   a clamp attached to said support member to receive and hold the tube; and
   a mechanism attaching said support member to said base so that said support member can be located in a plurality of positions at each of which the longitudinal axis is at different angle in a plane that intersects the surface of said base.

2. The apparatus as recited in claim 1 wherein said mechanism comprises a plurality of apertures in said base for receiving said support member, wherein an angle at which said support member extends from said base can be varied by placing said support member in different ones of said plurality of apertures.

3. The apparatus as recited in claim 1 wherein said support member pivotally extends from said base; and wherein said mechanism comprises a spring which biases said support member in one rotational direction, and a strut attached to said support member for engaging stops on said base.

4. The apparatus as recited in claim 1 wherein said mechanism comprises a spring loaded device for pivotally attaching said support member to said base and biasing said support member in one rotational direction; and a strut attached to said support member for engaging stops on said base.

5. The apparatus as recited in claim 1 wherein said clamp includes a device that releasably attaches to said support member so that said clamp may be positioned at different locations on said support member.

6. An apparatus for enabling a patient, having a tube extending from an arm, to administer a pharmaceutical through the tube, said apparatus comprising:
   a support member;
   a clamp attached to said support member to receive the tube; and
   a base on which the patient rests the arm during use of the apparatus and having a surface with a plurality of apertures for receiving said support member, each aperture having a longitudinal axis at a different angle with respect to the surface so that said support member can be rigidly positioned at a plurality of different angles with respect to the surface.

7. The apparatus as recited in claim 6 wherein said clamp includes a device that releasably attaches to said support member so that said clamp may be positioned at different locations on said support member.

8. An apparatus for enabling a patient, with a tube extending an arm, to administer a pharmaceutical through the tube, said apparatus comprising:
   a base on which the patient rests the arm during use of the apparatus;
   a support member attached to said base and rotatable with respect to said base;
   a strut attached to said support member for engaging stops on said base to hold said support member in a given position against a bias provided by said spring; and
   a clamp attached to said support member to receive the tube.

9. The apparatus as recited in claim 8 further comprising a spring which biases said support member in one rotational direction.

10. The apparatus as recited in claim 8 wherein said support member has a L-shape with a first leg to which said clamp is attached and a second leg attached to said base by a bracket; and further comprising a torsion spring wrapped around the second leg and bias said support member in one rotational direction.

11. The apparatus as recited in claim 8 wherein said clamp includes a device that releasably attaches to said support member so that said clamp may be positioned at different locations on said support member.

12. The apparatus as recited in claim 8 wherein said support member has one end fixedly attached to said base, and a joint that permits another end of said support member to move away from the base 62.

13. The apparatus as recited in claim 8 wherein said support member has one end fixedly attached to said base, and a resilient joint that permits another end of said support member to move away from the base 62.

* * * * *